US011884937B2

(12) United States Patent
Cooke et al.

(10) Patent No.: US 11,884,937 B2
(45) Date of Patent: *Jan. 30, 2024

(54) ACTIVATION OF INNATE IMMUNITY FOR ENHANCED NUCLEAR REPROGRAMMING OF SOMATIC CELLS WITH MRNA

(71) Applicant: The Board of Trustees of the Leland Stanford Junior University, Stanford, CA (US)

(72) Inventors: John P. Cooke, Houston, TX (US); Eduard Yakubov, Houston, TX (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 635 days.

This patent is subject to a terminal disclaimer.

(21) Appl. No.: 16/986,071

(22) Filed: Aug. 5, 2020

(65) Prior Publication Data

US 2021/0130792 A1 May 6, 2021

Related U.S. Application Data

(60) Continuation of application No. 15/479,979, filed on Apr. 5, 2017, now Pat. No. 10,760,061, which is a division of application No. 14/615,955, filed on Feb. 6, 2015, now Pat. No. 9,738,873.

(60) Provisional application No. 61/937,923, filed on Feb. 10, 2014.

(51) Int. Cl.
  *C12N 5/074* (2010.01)

(52) U.S. Cl.
  CPC ........ *C12N 5/0696* (2013.01); *C12N 2501/04* (2013.01); *C12N 2501/60* (2013.01); *C12N 2501/602* (2013.01); *C12N 2501/603* (2013.01); *C12N 2501/604* (2013.01); *C12N 2501/606* (2013.01); *C12N 2501/608* (2013.01); *C12N 2501/90* (2013.01); *C12N 2501/998* (2013.01); *C12N 2506/09* (2013.01); *C12N 2506/28* (2013.01)

(58) Field of Classification Search
  None
  See application file for complete search history.

(56) References Cited

U.S. PATENT DOCUMENTS

| 9,738,873 | B2* | 8/2017 | Cooke | C12N 5/0696 |
| 10,760,061 | B2* | 9/2020 | Cooke | C12N 5/0696 |
| 2008/0124365 | A1 | 5/2008 | Kim | |
| 2011/0143436 | A1 | 6/2011 | Dahl et al. | |
| 2013/0165504 | A1 | 6/2013 | Bancel et al. | |
| 2013/0189741 | A1 | 7/2013 | Meis et al. | |
| 2013/0202649 | A1 | 8/2013 | Cooke et al. | |
| 2013/0236974 | A1 | 9/2013 | Fougerolles | |
| 2013/0245106 | A1 | 9/2013 | Fougerolles et al. | |

FOREIGN PATENT DOCUMENTS

| WO | WO2008124133 | 10/2008 |
| WO | WO2011/071936 | 6/2011 |
| WO | WO2013109763 | 7/2013 |

OTHER PUBLICATIONS

Mandal, et al. (2013) "Reprogramming human fibroblasts to pluripotency using modified mRNA", Nature Protocols, 8(3): 568-82. (Year: 2013).*
Cary, et al. (2009) "Reprogramming of murine and human somatic cells using a single polycistronic vector" Proceedings of the National Academy of Science, USA., 106(1): 157-62. (Year: 2009).*
Warren, et al. (2010) "Highly Efficient Reprogramming to Pluripotency and Directed Differentiation of Human Cells with Synthetic Modified mRNA", Cell Stem Cell, 7: 618-30. (Year: 2010).*
Lee, et al. (2012) "Activation of Innate Immunity Is Required for Efficient Nuclear Reprogramming", Cell, 151: 547-58. (Year: 2012).*
Lee et al., "Activation of innate immunity is required for efficient nuclear reprogramming", CeiL Oct. 26, 2012, pp. 547-558, vol. 151, Issue 3, Elsevier Inc., Amsterdam, Netherlands.
Li et al, "Conversion of human fibroblasts to functional endothelial cells by defined factors", Arterioscler Thromb Vase ioL, May 15, 2013, pp. 1366-1375, 33(6), American Heart Association, Inc., Dallas, TX.
Rufaihah et al, "Human induced pluripotent stem cell-derived endothelial cells exhibit functional heterogeneity", Am Transl Res., Jan. 30, 2013, pp. 21-35, 5(1), AJTR, Madison, WL.
Marchand et al, "Concurrent generation of functional smooth muscle and endothelial cells via a vascular progenitor", Stem Cells TranslMed., 2014, pp. 91-97, 3(1), AlphaMed Press, Durham, NC.
Sayed et al, "Trans differentiation of human fibroblasts to endothelial cells: role of innate immunity", Circulation, Jan. 20, 2015, pp. 300-309, 131(3), American Heart Association, Inc., Dallas, TX.
Wong et al, "Therapeutic trans differentiation of human fibroblasts into endothelial cells using forced expression of lineage-specific transcription factors", J Tissue Eng., Feb. 16, 2016, pp. 1-10, vol. 7, Wiley, Hoboken, NJ.
Zhou et al, "Optimal ROS Signaling Is Critical for Nuclear Reprogramming", Cell Rep., May 3, 2016, pp. 919-925, vol. 15, Issue 5, Elsevier Inc., Amsterdam, Netherlands.
Meng et al, "Trans differentiation Requires iNOS Activation: Role of RING1A S-Nitrosylation", Circ Res., Sep. 3, 2016, pp. e129-e138, vol. 119, Issue 9, American Heart Association, Inc., Dallas, TX.
Clayton et al, "A comparison of the pro-angiogenic potential of human induced pluripotent stem cell derived endothelial cells and induced endothelial cells in a murine model of peripheral arterial disease", Int J Cardio, May 1, 017, p. 81-89, vol. 234, Elsevier Inc., Amsterdam, Netherlands.

(Continued)

Primary Examiner — Robert M Kelly
(74) Attorney, Agent, or Firm — Pamela J. Sherwood; Bozicevic, Field & Francis LLP

(57) ABSTRACT

The nuclear reprogramming of somatic cells with mRNA encoding reprogramming factors is shown to be greatly accelerated by activation of innate immune responses in the somatic cell. Methods of activating innate immunity include activation of PKR, of toll-like receptors, e.g. TLR3, etc. In some embodiments the mRNA provides the activator of innate immunity.

12 Claims, 6 Drawing Sheets

(56) References Cited

OTHER PUBLICATIONS

Sayed et al, "Retinoic Acid Inducible Gene 1 Protein {RIG1)-Like Receptor Pathway Is Required for Efficient Nuclear R-programming", Stem Cells, May 2017, pp. 1197-1207, vol. 35, Issue 5, Wiley, Hoboken, NJ.

Sayed et al, "Therapeutic Trans differentiation: Can we Generate Cardiac Tissue Rather Than Scar after Myocardial injury?", Houston Methodist Debakey Cardiovascular J., Oct. 2, 2013, pp. 210-212, vol. 9, No. 4, Houston Methodist DeBakey Heart & Vascular Center, Houston, TX.

Wong et al., "Induced Pluripotent Stem Cells: How they will change the practice of Cardiovascular Medicine", Houston Methodist Debakey Cardiovascular J., Oct. 2013, pp. 206-209, vol. 9, No. 4, Houston Methodist peBakey Heart & Vascular Center, Houston, TX.

Cooke et al., "Innate immunity and epigenetic plasticity in cellular reprogramming", Curr Opin Genet Dev., October I>014, pp. 89-91, vol. 28, Elsevier Inc., Amsterdam, Netherlands.

Connell et al., "Therapeutic Trans differentiation: A novel approach for ischemic syndrome", Houston Methodist pebakey Cardiovascular J., Sep. 2015, pp. 176-179, vol. 11, No. 3, Houston Methodist DeBakey Heart & Vascular Center, Houston, TX.

Cooke et al., "Therapeutic trans differentiation: a novel approach for vascular disease", Circ Res., Mar. 1, 2013, pp. 748-750, 112(5), American Heart Association, Inc., Dallas, TX.

Yakubov et al. "Reprogramming of human fibroblasts to pluripotent stem cells using mRNA of four transcription actors", Biochemical and Biophysical Research Communications, Mar. 26, 2010, pp. 189-193, 394(1), Elsevier nc., Amsterdam, Netherlands.

Lee et al. "Activation of Innate Immunity Is Required for Efficient Nuclear Reprogramming", Cell, Oct. 26, 2012, pp. 547-558, 151(3), Elsevier Inc., Amsterdam, Netherlands.

Pearce et al., "Metabolic Pathways in Immune Cell Activation and Quiescence", Immunity, Apr. 18, 2013, pp. 33-643, 38(4), Elsevier Inc., Amsterdam, Netherlands.

Kariko et al., "Incorporation of Pseudo uridine Into mRNA Yields Superior Non immunogenic Vector With Increased translational Capacity and Biological Stability", Molecular Therapy, Nov. 2008, pp. 1833-1840, 16(11 ), The American Society of Gene Therapy, Milwaukee, WI.

Pan et al., "Bacterial LPS up-regulated TLR3 expression is critical for antiviral response in human monocytes: evidence for negative regulation by CYLD", International Immunology, Apr. 15, 2011, pp. 357-364, 23(6), The Japanese Society for Immunology,Tokyo, Japan.

Tam et al. "The Molecular Basis of Aging in Stem Cells" Mechanisms of Aging and Development, Jan. 2007, pp. 137-148, vol. 128, No. 1, Elsevier Inc., Amsterdam, Netherlands.

Hou et al., "Optimal ROS Signaling Is Critical for Nuclear Reprogramming", Cell Rep., May 3, 2016, pp. 919-925, vol. 15, Issue 5, Elsevier Inc., Amsterdam, Netherlands.

Takahashi, et al. (2006) "Induction of Pluripotent Stem Cells from Mouse Embryonic and Adult Fibroblast Cultures by Defined Factors", Cell, 126: 663-76.

Warren et al., "Highly Efficient Reprogramming to Pluripotency and Directed Differentiation of Human Cells with synthetic Modified mRNA", Cell Stem Cell, Nov. 5, 2010, pp. 618-630, 7(5), Elsevier Inc., Amsterdam, Netherlands.

* cited by examiner

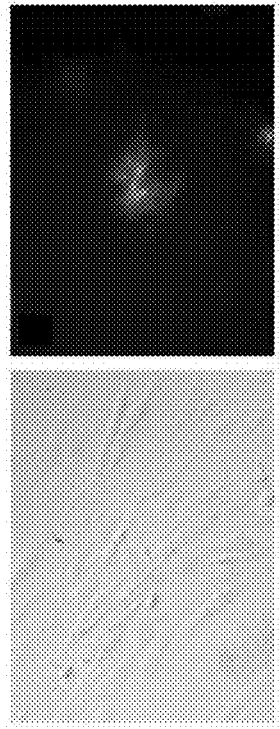
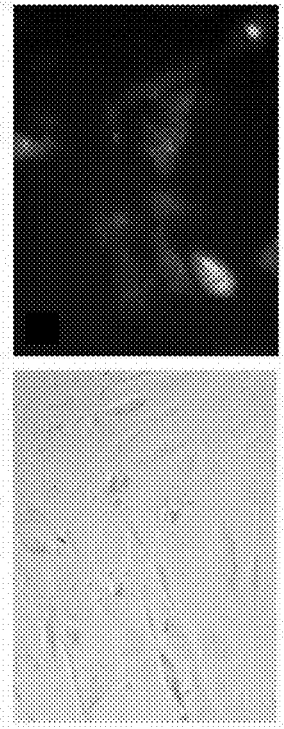
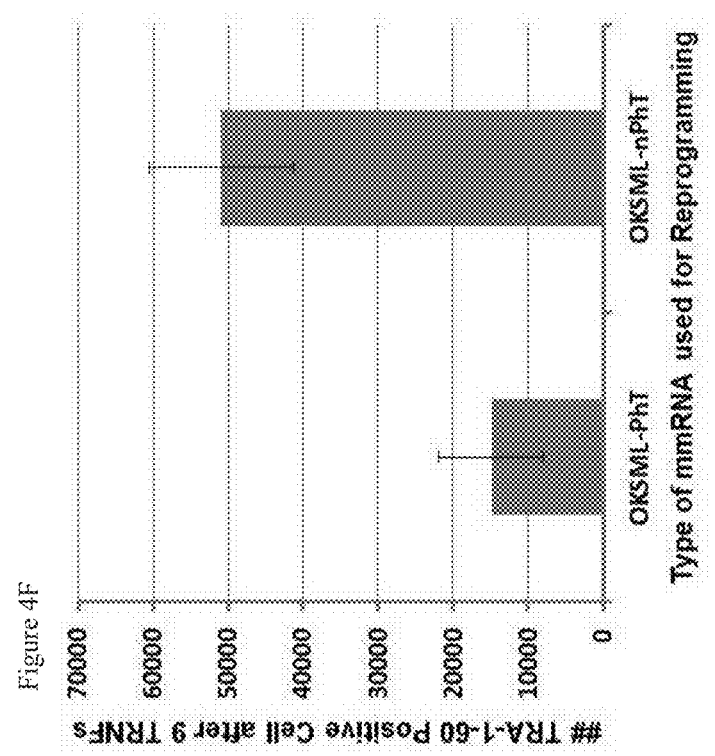

ACTIVATION OF INNATE IMMUNITY FOR ENHANCED NUCLEAR REPROGRAMMING OF SOMATIC CELLS WITH MRNA

CROSS REFERENCE

This application claims benefit and is a Continuation of application Ser. No. 15/479,979 filed Apr. 5, 2017, now U.S. Pat. No. 10,760,061, issued Sep. 1, 2020, which is a Divisional of application Ser. No. 14/615,955 filed Feb. 6, 2015, now U.S. Pat. No. 9,738,873 issued on Aug. 22, 2017 which claims benefit of U.S. Provisional Patent Application No. 61/937,923, filed Feb. 10, 2014, which applications are incorporated herein by reference in their entirety.

FEDERALLY SPONSORED RESEARCH AND DEVELOPMENT

This invention was made with Government support under contract HL100397 awarded by the National Institutes of Health. The Government has certain rights in the invention.

BACKGROUND OF THE INVENTION

Seminal studies by Yamanaka and colleagues revealed that ectopic expression of certain transcriptional factors could induce pluripotency in somatic cells. These induced pluripotent stem cells (iPSC) self-renew and differentiate into a wide variety of cell types, making them an appealing option for disease- and patient-specific regenerative medicine therapies. They have been used to successfully model human disease and have great potential for use in drug screening and patient-specific cell therapy. Furthermore, iPSCs generated from diseased cells can serve as useful tools for studying disease mechanisms and potential therapies. However, much remains to be understood about the underlying mechanisms of reprogramming of somatic cells to iPSCs, and there is concern regarding potential clinical applications in the absence of mechanistic insights.

The set of factors (RFs) for reprogramming to pluripotency include Oct3/4, Sox2, cMyc, Klf4, Lin28, and Nanog. Oct3/4 and Sox2 are transcription factors that maintain pluripotency in embryonic stem (ES) cells while Klf4 and c-Myc are transcription factors thought to boost iPSC generation efficiency. The transcription factor c-Myc is believed to modify chromatin structure to allow Oct3/4 and Sox2 to more efficiently access genes necessary for reprogramming while Klf4 enhances the activation of certain genes by Oct3/4 and Sox2. Nanog, like Oct3/4 and Sox2, is a transcription factor that maintains pluripotency in ES cells while Lin28 is an mRNA-binding protein thought to influence the translation or stability of specific mRNAs during differentiation. Recently, it has been shown that retroviral expression of Oct3/4 and Sox2, together with co-administration of valproic acid, a chromatin destabilizer and histone deacetylase inhibitor, is sufficient to reprogram fibroblasts into iPSCs.

To generate iPSCs from somatic cells, viral vectors or plasmids have been used to overexpress some combination of these reprogramming factors. However, these methods result in a low efficiency of reprogramming and fail to provide precise control of the reprogramming process. Furthermore, these methods for nuclear reprogramming inherently raise concerns about potential tumorigenicity and gene-silencing mutations caused by DNA integration. The integration of foreign DNA into the host genome from retroviral infection raises concerns that the integration of foreign DNA could silence indispensable genes or induce dysregulation of these genes. While Cre-LoxP site gene delivery or PiggyBac transposon approaches have been used to excise foreign DNA from the host genome following gene delivery, neither strategy eliminates the risk of mutagenesis because they leave a small insert of residual foreign DNA.

Recently, another form of nuclear reprogramming has involved the transdifferentiation of one somatic cell to another, using a similar approach as in generating iPSCs. However, in this case, most investigators have used exogenous DNA encoding lineage specific transcription factors. One can also employ conditional expression of the Yamanaka factors to induce "partially reprogrammed" cells, and then maintain the cells in medium that favors the generation of the somatic cell of interest. See Ginsberg et al. (2012) Cell 151(3):559-75; and Li et al. (2013) Arterioscler Thromb Vasc Biol. 33(6):1366-75.

Another form of nuclear reprogramming is related to telomere extension. Generally, somatic cells do not have telomerase activity. One can employ an activator of innate immunity and the telomerase enzyme and/or its RNA subunit TERC, to increase telomere length. In this case, the activator of innate immunity enhances the telomere extension as it increases endogenous telomerase activity and/or increases epigenetic plasticity so that the telomerase enzyme can interact more efficiently with the telomeric region of the chromosomes.

As an alternative to reprogramming with foreign DNA, approaches have been developed that transfer mRNA encoding reprogramming factors into somatic cells. A mmRNA based approach for iPSC generation or transdifferentiation to a different somatic cell type avoids concerns for integration of foreign DNA, and provides for greater control over the concentration, timing, and sequence of factor stimulation. Cytosolic delivery of mRNA into mammalian cells can be achieved using electroporation or by complexing the RNA with a cationic vehicle to facilitate uptake by endocytosis, or by incorporating the RNA in exosomes, nanoparticles or microparticles. See, for example Warren et al. (2010) Cell Stem Cell 7(5):618-630, review by Mandal and Rossi (2013) Nat. Protocol. 8(3):568-582; and Yakubov et al. (2010) Biochem Biophys Res Commun. 394(1):189-93. To enhance the functionality activity of the mRNA, synthetic messenger RNAs have incorporated modifications designed to bypass innate immune responses. Using In Vitro Co-Transcription capping reactions, synthetic mRNA for these purposes typically incorporates a chemically synthesized 5' guanine cap which is a structural homolog of the natural 7-methylguanosine [m7G(5')] cap. This commonly used type of in vitro Transcription (IVT) reaction, however, yields a significant fraction of uncapped RNA products primed with 5' guanine triphosphates which resembles some viral and bacterial RNAs (see Lippincott Williams & Wilkins, Philadelphia, PA, ed. 5, 2007; and Bieger et al. (1989) J. Bacteriol. 171:141. These RNA products can induce innate immune signaling as they are detected sensors for 5' triphosphate ssRNA, see Fields Virology, D. Knipe, P. M. Howley, Eds.

Prior art approaches have sought to reduce the immunogenic profile of synthetic RNA by treatment with phosphatase in order to reduce activation of antiviral and bacterial defenses by single stranded 5' triphosphate RNA. Additional modifications to reduce innate immune responses to transfected RNA can include the incorporation of modified ribonucleoside bases, for example 5-methylcytidine (5mC) for cytidine, and/or pseudouridine (psi) for uridine.

The cells can also be grown in media supplemented with a type I interferon decoy receptor, for example the vaccinia B18R protein.

However significant problems have remained in the actual practice of such methods. The present invention addresses this issue.

SUMMARY OF THE INVENTION

Compositions and methods are provided for efficient generation of induced pluripotential cells or transdifferentiated cells, or somatic cells with lengthened telomeres, using non-integrating methods, particularly mRNA based methods. In the methods of the invention, a somatic cell for which reprogramming to pluripotency or transdifferentiation is desired is contacted with an effective dose of an activator of innate immunity, particularly an activator of the PKR pathway, or sensors of pathogen associated molecular patterns (such as toll-like receptors, eg.TLR3) and/or damage associated molecular patterns (such as RAGE). The contacting step may be performed before, concurrently with, or following contact of the cell with non-integrating reprogramming factors, usually concurrently. Non-integrating reprogramming factors are provided as mRNA encoding nuclear-acting polypeptides that alter transcription and induce reprogramming in targeted cells. In some embodiments the reprogramming factor is mRNA encoding one or more of Oct3/4, Sox2, c-Myc, Klf4, Lin28, and Nanog. In some embodiments, the reprogramming factors are mRNA encoding lineage-specific transcription factors that enhance transdifferentiation to another somatic cell type. In some embodiments, the reprogramming factors are mRNA encoding telomerase, and/or its RNA subunit TERC, and/or telomere associated proteins (e.g. the shelterin proteins). Conveniently the activation of innate immunity is provided by the mRNA itself.

In some embodiments of the invention, the mRNA for reprogramming is a modified mRNA (mmRNA) composition encoding one or a cocktail of reprogramming factors and comprising one or more modifications, such as unnatural nucleotides. In some embodiments a portion of the mmRNA composition comprises a 5' triphosphate, which provides an activator of innate immunity. The portion of the composition that comprises a 5' triphosphate may be up to about 1%, up to about 5%, up to about 10%, up to about 15%, up to about 20%, up to about 25%, up to about 30%, up to about 50%, up to about 75% and may be substantially all of the mmRNA. In some embodiments, the portion of mmRNA comprising a 5' triphosphate is from about 5% to about 25%, and the balance of mmRNA in the composition comprises a cap structure at the 5' end. The cap structure can be a native 7-methylguanylate cap, or a cap analog, for example anti-reverse cap analog (ARCA), 3"-O-Me-m7G (5')ppp(5')G, (m7G(5")ppp(5')G), etc.

In other embodiments, a mmRNA composition lacking a 5' triphosphate, e.g. by introduction of a 5' cap, phosphatase treatment, etc., is combined with a small molecule activator of PKR, including without limitation dsRNA, mRNA not encoding a reprogramming factor and comprising a 5' triphosphate; and the like.

In other embodiments, kits are provided for nuclear reprogramming of somatic cells. Such kits may comprise an mmRNA composition or reagents for in vitro transcription thereof, encoding one or a cocktail of reprogramming factors e.g. SOX2, OCT4, Nanog, KLF4, cMYC, and the like. Such kits may alternatively or in combination provide one or a cocktail of factors useful in transdifferentiating cells to a lineage of interest. For example, an endothelial transdifferentiation kit may comprise one or more of RNA (e.g. poly I:C) so as to activate innate immunity, and the growth factors BMP4, VEGF, bFGF, and/or the small molecules 8-Br-cAMP, SB431542, etc. Such kits may further comprise suitable buffers, cell growth medium, instructions and the like necessary to perform the methods of the invention. an activator of innate immunity, e.g. one or more TLR agonists, including without limitation double stranded nucleic acids, such as poly I:C.

BRIEF DESCRIPTION OF THE DRAWINGS

FIG. 4A-4F. Reprogramming of BJ-FBs with nPhT OKSML mmRNA is more efficient then with PhT mmRNA.

DETAILED DESCRIPTION OF THE EMBODIMENTS

Figure 1:
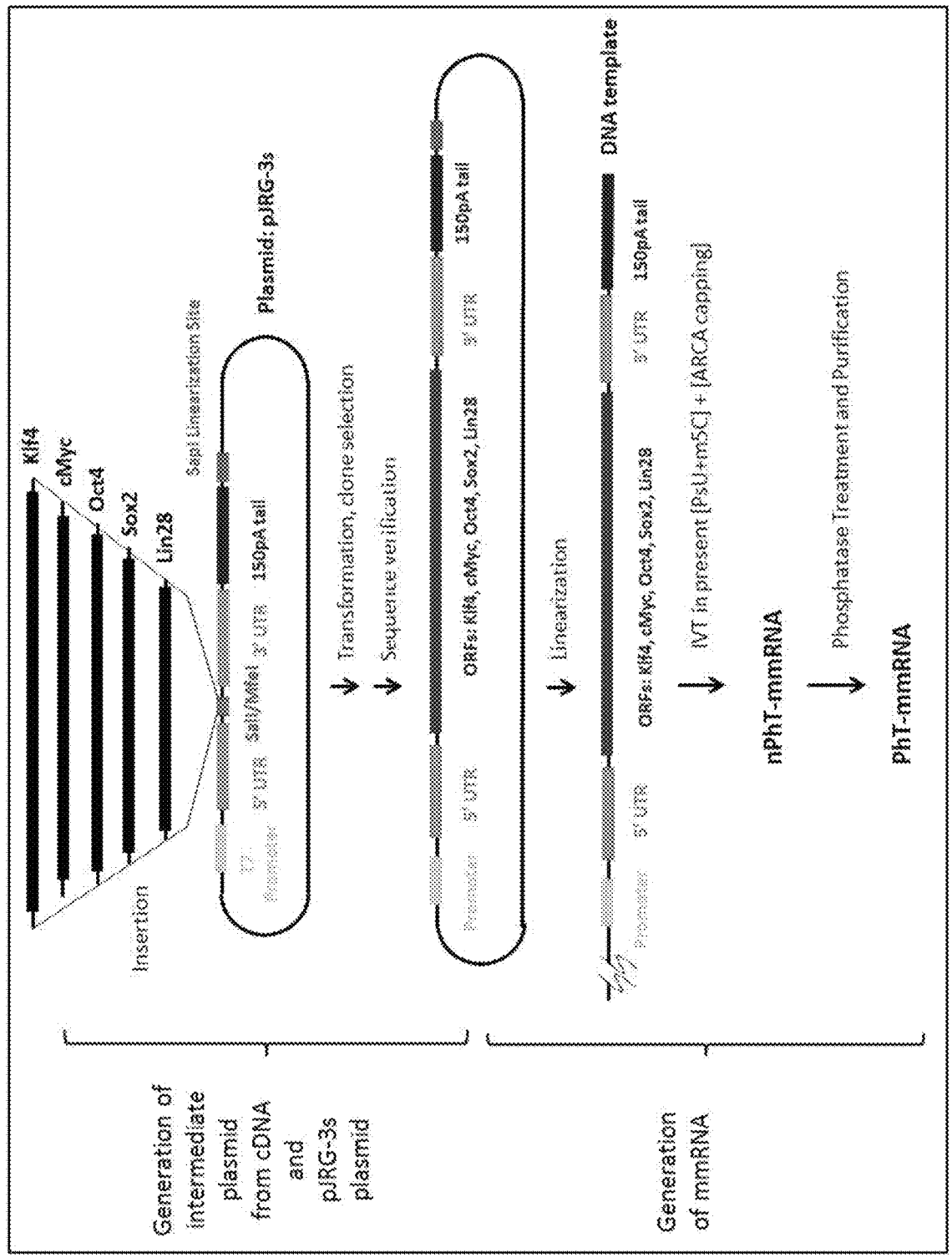
FIG. 1. nPhT- and PhT-mmRNAs mmRNA generation.
Figure 2:
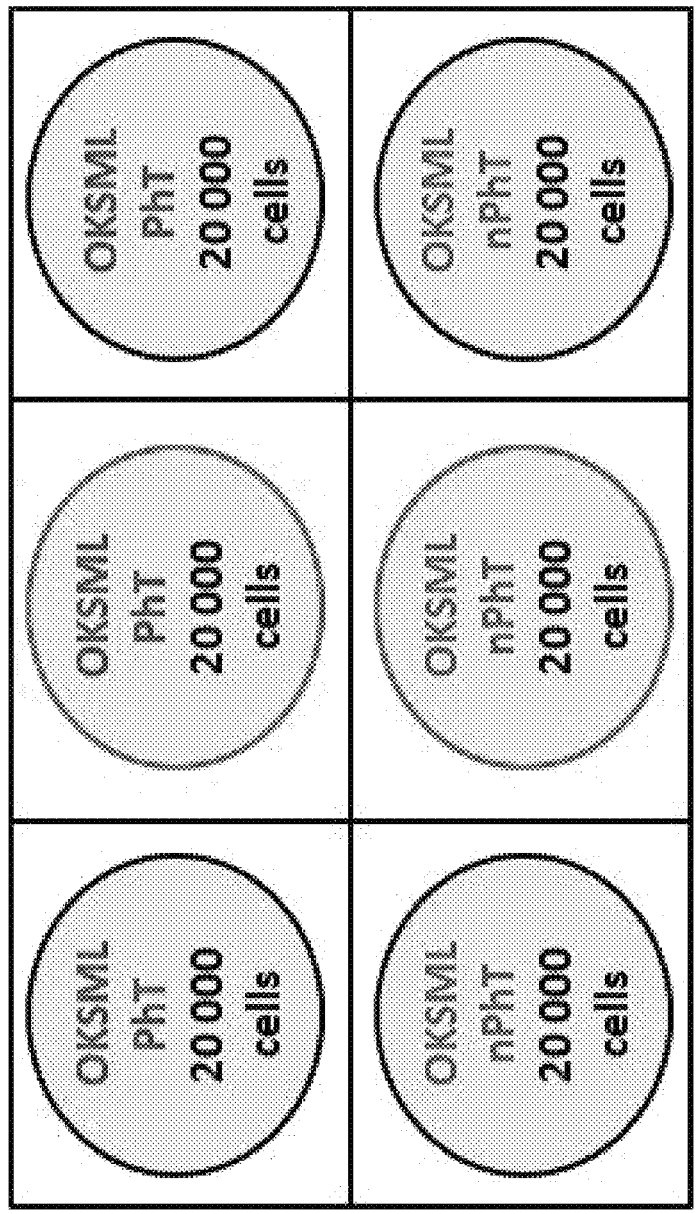
FIG. 2. Description of Experimental Setting.
Figure 3:
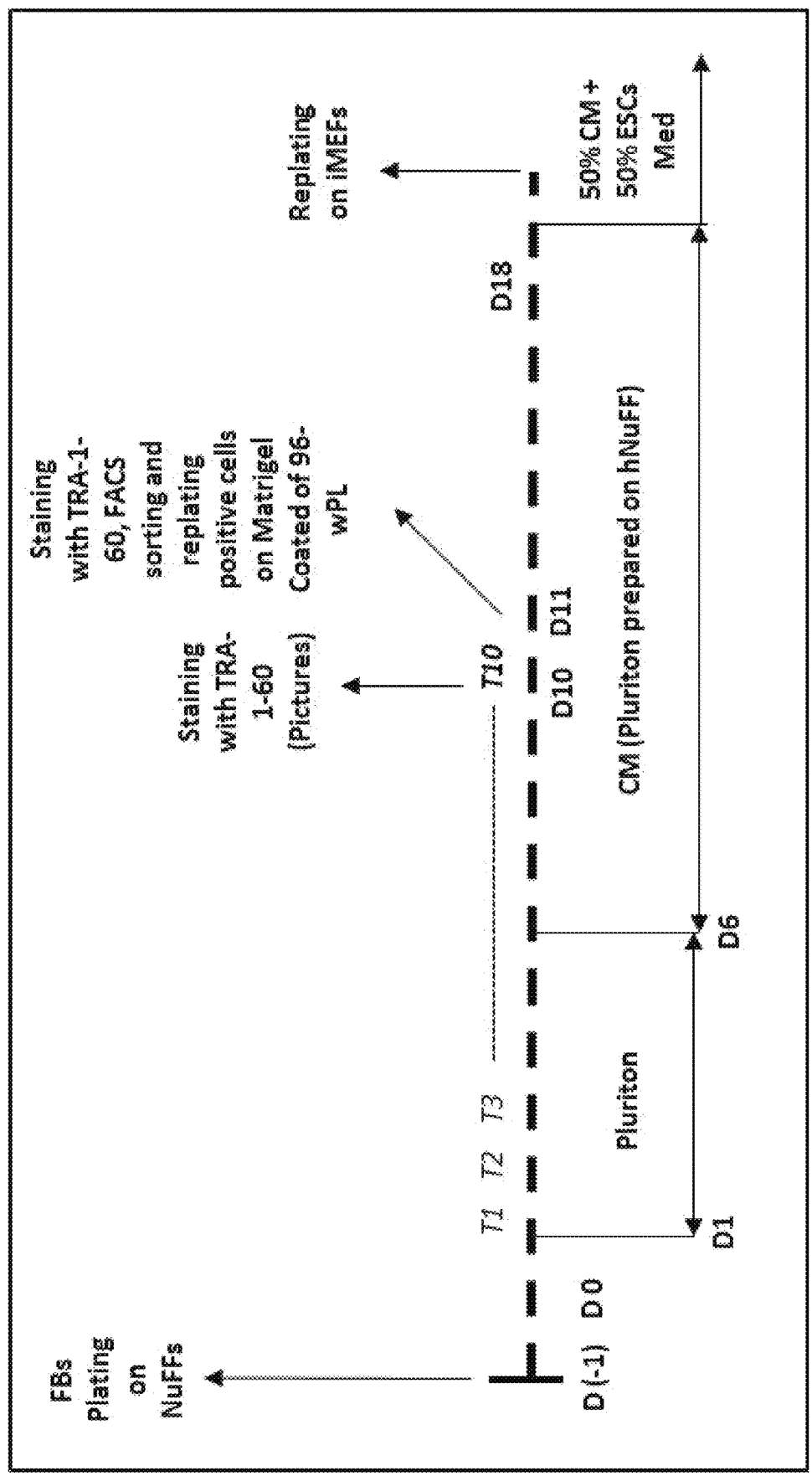
FIG. 3. Schematic of Reprogramming of BJ-FBs using nPhT-mmRNA and PhT-mmRNA.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

Innate Immunity. The innate immune system is a primitive cellular response that provides for the response of cells to pathogens, stress, or cellular damage. Recognition of these antigens by the innate immune system may result in an inflammatory response characterized by the production of cytokines such as TNF, IL-1, IL-6, and IL-8; as well as gene activation of ICAM-1 and E-selectin, among others.

The broad classes of pathogens, e.g. viruses, bacteria, and fungi, may constitutively express a set of class-specific, mutation-resistant molecules called pathogen-associated molecular patterns (PAMPs). These microbial molecular markers may be composed of proteins, carbohydrates, lipids, nucleic acids and/or combinations thereof, and may be located internally or externally. Examples include the endotoxin lipopolysaccharide (LPS), single or double-stranded RNA, and the like. Furthermore, cellular stress or damage (e.g. as generated by significant changes in pH, oxygen, or other environmental or chemical insults) can generate damage associated molecular patterns (DAMPs) that are detected by receptors such as RAGE, for example see Tang et al. (2012) Immunol Rev. 249(1):158-75.

Protein kinase RNA-activated, also known as protein kinase R (PKR), is an interferon-induced, double-stranded RNA-activated protein kinase. PKR is activated by double-stranded RNA (dsRNA). It contains an N-terminal dsRNA binding domain (dsRBD) and a C-terminal kinase domain, that gives it pro-apoptotic (cell-killing) functions. Binding to dsRNA is believed to activate PKR by inducing dimerization and subsequent auto-phosphorylation reactions. Once active, PKR is able to phosphorylate the eukaryotic translation initiation factor EIF2A. This inhibits further cellular mRNA translation, thereby preventing viral protein synthesis. Active PKR is also able to mediate the activation of the transcription factor NFκB, by phosphorylating its inhibitory subunit, IκB. Activated NFκB upregulates the expression of interferons, which work to spread the antiviral signal locally.

PKR agonists of particular interest include mRNA comprising a 5' triphosphate. Such mRNA can be synthesized by in vitro synthesis.

The Toll-like receptors are type I transmembrane (TM) proteins that function as pattern recognition receptors (PRR)s that possess varying numbers of extracellular N-terminal leucine-rich repeat (LRR) motifs, followed by a cysteine-rich region, a TM domain, and an intracellular Toll/IL-1 R (TIR) motif. The LLR domain is important for ligand binding and associated signaling and is a common feature of PRRs. The TIR domain is important in protein-protein interactions and is typically associated with innate immunity. The TIR domain also unites a larger IL-1 R/TLR superfamily that is composed of three subgroups. The human TLR family is composed of at least 10 members, TLR1 through 10. Each TLR is specific in its expression patterns and PAMP sensitivities.

Toll-like receptor 3 (TLR3) recognizes double-stranded RNA (dsRNA) and mimetics thereof, a molecular pattern associated with viral infection. It maps to chromosome 4q35 and its sequence encodes a putative 904 aa protein with 24 N-terminal LRRs and a calculated molecular weight of 97 kDa. TLR3 is most closely related to TLR5, TLR7, and TLR8, each with 26% overall aa sequence identity. TLR3 mRNA is elevated after exposure to Gram-negative bacteria and to an even greater extent in response to Gram-positive bacteria.

TLR3 specifically recognizes double-stranded RNA (dsRNA) and induces multiple intracellular events responsible for innate antiviral immunity against a number of viral infections. The predicted 904-amino acid TLR3 protein contains the characteristic Toll motifs: an extracellular leucine-rich repeat (LRR) domain and a cytoplasmic interleukin-1 receptor-like region.

Exposure to double-stranded RNA (dsRNA) or polyinosine-polycytidylic acid (poly(I:C)), a synthetic dsRNA analog, induces the production of interferon α and β and by signaling through TLR3 activates NFκB. IRF3 is specifically induced by stimulation of TLR3 or TLR4, which mediates a specific gene program responsible for innate antiviral responses. TRIF is necessary for TLR3-dependent activation of NFκB. It serves as an adaptor protein linking RIP1 and TLR3 to mediate TLR3-induced NFκB activation.

RIG-1 (retinoic acid-inducible gene 1) is a RIG-I-like receptor dsRNA helicase enzyme that is encoded (in humans) by the DDX58 gene. RIG-I is part of the RIG-I-like receptor (RLR) family, which also includes MDA5 and LGP2, and functions as a pattern recognition receptor that is a sensor for viruses. RIG-I typically recognizes short (<4000nt) 5' triphosphate dsRNA. RIG-I and MDA5 are involved in activating MAVS and triggering an antiviral response. The human RIG1 gene may be accessed at Genbank NM_014314.3 and the protein at Genbank NP_055129.2.

Toll-like receptor 4 is a protein that in humans is encoded by the TLR4 gene. It detects lipopolysaccharide from Gram-negative bacteria and is thus important in the activation of the innate immune system. This receptor is most abundantly expressed in placenta, and in myelomonocytic subpopulation of the leukocytes. The human TLR4 gene may be accessed at Genbank NM_003266.3 and the protein accessed at Genbank NP_003257.1.

Activation of TLR4 leads to downstream release of inflammatory modulators including TNF-α and Interleukin-1. Agonists include morphine, oxycodone, fentanyl, methadone, lipopolysaccharides (LPS), carbamazepine, oxcarbazepine, etc.

TLR agonist. TLR agonists activate TLRs, including without limitation TLR3, TLR4, and RIG1. Examples of TLR agonists include pathogen-associated molecular patterns (PAMPs) and mimetics thereof. These microbial molecular markers may be composed of proteins, carbohydrates, lipids, nucleic acids and/or combinations thereof, and may be located internally or externally, as known in the art. Examples include LPS, zymosan, peptidoglycans, flagellin, synthetic TLR2 agonist Pam3cys, Pam3CSK4, MALP-2, Imiquimod, CpG ODN, and the like.

TLR3 agonists include double-stranded RNA; Poly(I:C), Poly(A.U), etc., where such nucleic acids usually have a size of at least about 10 bp, at least about 20 bp, at least about 50 bp and may have a high molecular weight of from about 1 to about 20 kb, usually not more than about 50 to 100 kb. Alternative TLR3 agonists may directly bind to the protein, e.g. antibodies or small molecules that selectively bind to and activate TLR3. Other TLR3 agonists include retroviruses, e.g. a retrovirus engineered to lack the ability to integrate into the genome.

The dose of agonist that is effective in the methods of the invention is a dose that increases the efficiency of reprogramming of a cell or cell population, relative to the same population in the absence of the PKR and/or TLR agonist. It will be understood that the mmRNA encoding reprogramming factors can also act as an activator of innate immunity by providing at least a portion of the mRNA with a 5' triphosphate/The term "reprogramming" as used here means nuclear reprogramming of a somatic cell to a pluripotential cell (eg. a fibroblast to an induced pluripotential cell) or nuclear reprogramming of a somatic cell to a substantially different somatic cell (eg. a fibroblast to an endothelial cell), in vitro or in vivo. The latter process is also known as transdifferentiation. Telomere extension itself may be considered another form of nuclear reprogramming. In addition, this process of telomere extension is also activated during nuclear reprogramming to pluripotency, see, for example, Lapasset et al. (2011) Genes Dev. 25(21):2248-53.

Conveniently, a marker of innate immune activation may be assessed for the determination of suitable doses, including the activation of NFκB in the somatic cells of interest for reprogramming, production of interferons α and β, and the like. For example, where the TLR agonist is poly I:C or an analog thereof, an effective dose may be at least about 10 ng/ml, at least about 50 ng/ml, at least about 100 ng/ml, at least about 250 ng/ml, at least about 500 ng/ml. An optimized concentration of poly I:C in culture medium is at least 10 ng/ml and not more than 3000 ng/ml, including a range from 20 ng/ml to 300 ng/ml, and particularly from 25 ng/ml to 150 ng/ml, for example around 30 ng/ml. The dose of a TLR agonist other than poly I:C may be calculated based on the provision of activity equivalent to the optimized poly I:C dose.

Modified mRNA (mmRNA) composition. In the methods of the invention, one form of nuclear reprogramming is accomplished by contacting somatic cells with a cocktail of mmRNA encoding reprogramming factors. The modified mRNA may be provided as a purified IVT transcript. Various combinations and ratios of reprogramming factors are known and used in the art, including, for example, for nuclear reprogramming of a somatic cell to pluripotency, one may use a cocktail comprising the five reprogramming factors (OKSML; Oct 4, KLF4, Sox2, cMyc and Lin28) in equimolar quantities except for Oct 4. For the nuclear reprogramming involved in transdifferentiation, an exemplary cocktail comprises the transcriptional factors ETV2, FLI1, and ERG1 for transdifferentiating a somatic cell into an endothelial cell, see Ginsberg et al. (2012) Cell 151(3): 559-75. Transdifferentiation of fibroblasts to endothelial cells can be accomplished using the TLR3 agonist (Poly I:C) given to activate innate immunity, combined with small molecules and growth factors, such as VEGF, FGF, 8Br-cAMP, and an inhibitor of the TGFβ receptor.

As known in the art, mmRNA may comprise one or more non-natural nucleotides. The nucleoside modification may include a compound selected from the group consisting of pyridin-4-one ribonucleoside, 5-aza-uridine, 2-thio-5-aza-uridine, 2-thiouridine, 4-thio-pseudouridine, 2-thio-pseudouridine, 5-hy-droxyuridine, 3-methyluridine, 5-carboxymethyluridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thiouridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine. 2-thio-dihydrouridine, 2-thiodihydropseudouridine, 2-methoxyuridine, 2-methoxy-4-thiouridine, 4-methoxy-pseudouridine, 4-methoxy-2-thio-pseudouridine, 5-azacytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebu larine, 5-aza-zebu larine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyadenosine, 2-methylthio-N-6-(cis-hydroxyisopentenyl) adenosine, N6-glycinylcarbamoyladenosine, N6-threonyl-carbamoyladenosine, 2-methylthio-N6-threonyl carbamoyladenosine, N6.N6-dimethyladenosine, 7-methyladenine, 2-methylthio-adenine, 2-methoxy-adenine, inosine, 1-me-thyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylgua-nosine, N2,N2-dimethylguanosine, 8-oxo-guanosine, 7-me-thyl-8-oxo-guanosine, 1-methyl-6-thio-guanosine, N2-methyl-6-thio-guano sine, and N2,N2-dimethyl-6-thio-guanosine.

In some embodiments, the modifications are independently selected from the group consisting of 5-methylcytosine, pseudouridine and 1-methylpseudouridine. Two modifications of the nucleic acid molecule may be located on nucleosides of the modified nucleic acid molecule. The modified nucleosides may be selected from 5-methylcytosine and pseudouridine.

The population of mmRNA may comprise 5' triphosphate on all or some of the mmRNA molecules. When reference is made to a "portion" of the population comprising a 5' triphosphate, it is intended that the population as a whole is considered. For example, when a cocktail of mRNA specificities is provided, the percentage of molecules with 5' triphosphate can be distributed between the specificities, or can be provided in a single specificity. The portion of the composition that comprises a 5' triphosphate may be up to about 1%, up to about 5%, up to about 10%, up to about 15%, up to about 20%, up to about 25%, up to about 30%, up to about 50%, up to about 75% and may be substantially all of the mmRNA. In some embodiments, the portion of mmRNA comprising a 5' triphosphate is from about 5% to about 25%, and the balance of mmRNA in the composition comprises a cap structure at the 5' end.

A 5' cap structure can be a native 7-methylguanylate cap, or a cap analog, for example anti-reverse cap analog (ARCA), 3"-O-Me-m7G(5')ppp(5')G, (m7G(5")ppp(5')G), Cap0, Cap1, inosine, N1-methyl-guanosine, 2' fluoro-guanosine, 7-deaza-guanosine, 8-oxo-guanosine, 2-amino-guanosine, LNA-guanosine, 2-azido-guanosine, etc.

Reprogramming factors, as used herein, refers to one or a cocktail of biologically active polypeptides that act on a cell to alter transcription, and which upon expression, reprogram a somatic cell a different cell type, or to multipotency or to pluripotency. In the special case of telomere extension using mmRNA encoding telomerase, TERC and/or telomere associated proteins, the targeted action to extend the telomere indirectly has global effects on the transcriptional profile that change a cell type from a senescent to a juvenile form, which is practically speaking a form of nuclear reprogramming, see Matsushita et al. (2001) Circ Res. 89(9):793-8. For the purposes of the present invention, the reprogramming factors are provided as mmRNA encoding the polypeptides described below.

In some embodiments the reprogramming factor is a transcription factor, including without limitation, Oct3/4; Sox2; Klf4; c-Myc; and Nanog. Also of interest as a reprogramming factor is Lin28, which is an mRNA-binding protein thought to influence the translation or stability of specific mRNAs during differentiation.

Reprogramming factors of interest also include factors useful in transdifferentiation, where a somatic cell is reprogrammed to a different somatic cell. For the purpose of transdifferentiation of one somatic cell to another, substantially different, somatic cell type, a different set of reprogramming factors find use. For example, to transdifferentiate a fibroblast to a cardiomyocyte, one might use Gata4, Mef2c and Tbx5 (see Cell, Volume 142, Issue 3, 375-386, 6 Aug. 2010, herein specifically incorporated by reference.)

A mmRNA composition of the invention may encode one or more biologically active reprogramming factors. The composition may comprise at least about 10 ng/µl each mmRNA specificity, (i.e. encoding each reprogramming factor), at least about 50 ng/µl; at least about 100 ng/µl, at least about 200 ng/µl, at least about 250 ng/µl, at least about 300 ng/µl, or more.

A Klf4 polypeptide is a polypeptide comprising the amino acid sequence that is at least 70% identical to the amino acid sequence of human Klf4, i.e., Kruppel-Like Factor 4 the sequence of which may be found at GenBank Accession Nos. NP_004226 and NM_004235. Klf4 polypeptides, e.g. those that are at least 70%, 75%, 80%, 85%, 90%, 91%, 92%, 95%, 97%, 99%, or 100% identical to the sequence provided in GenBank Accession No. NM_004235. The nucleic acids that encode them find use as a reprogramming factor in the present invention.

A c-Myc polypeptide is a polypeptide comprising an amino acid sequence that is at least 70% identical to the amino acid sequence of human c-Myc, i.e., myelocytomatosis viral oncogene homolog, the sequence of which may be found at GenBank Accession Nos. NP_002458 and NM_002467. c-Myc polypeptides, e.g. those that are at least 70%, 75%, 80%, 85%, 90%, 91%, 92%, 95%, 97%, 99%, or 100% identical to the sequence provided in GenBank Accession No. NM_002467. The nucleic acids that encode them find use as a reprogramming factor in the present invention.

A Nanog polypeptide is a polypeptide comprising an amino acid sequence that is at least 70% identical to the amino acid sequence of human Nanog, i.e., Nanog homeobox, the sequence of which may be found at GenBank Accession Nos. NP_079141 and NM_024865. Nanog polypeptides, e.g. those that are at least 70%, 75%, 80%, 85%, 90%, 91%, 92%, 95%, 97%, 99%, or 100% identical to the sequence provided in GenBank Accession No. NM_024865. The nucleic acids that encode them find use as a reprogramming factor in the present invention.

A Lin-28 polypeptide is a polypeptide comprising an amino acid sequence that is at least 70% identical to the amino acid sequence of human Lin-28, i.e., Lin-28 homolog of *C. elegans*, the sequence of which may be found at GenBank Accession Nos. NP_078950 and NM_024674. Lin-28 polypeptides, e.g. those that are at least 70%, 75%, 80%, 85%, 90%, 91%, 92%, 95%, 97%, 99%, or 100% identical to the sequence provided in GenBank Accession No. NM_024674. The nucleic acids that encode them find use as a reprogramming factor in the present invention.

An Oct3/4 polypeptide is a polypeptide comprising an amino acid sequence that is at least 70% identical to the amino acid sequence of human Oct 3/4, also known as *Homo sapiens* POU class 5 homeobox 1 (POU5F1) the sequence of which may be found at GenBank Accession Nos. NP_002692 and NM_002701. Oct3/4 polypeptides, e.g. those that are at least 70%, 75%, 80%, 85%, 90%, 91%, 92%, 95%, 97%, 99%, or 100% identical to the sequence provided in GenBank Accession No. NM_002701. The nucleic acids that encode them find use as a reprogramming factor in the present invention.

A Sox2 polypeptide is a polypeptide comprising the amino acid sequence at least 70% identical to the amino acid sequence of human Sox2, i.e., sex-determining region Y-box 2 protein, the sequence of which may be found at GenBank Accession Nos. NP_003097 and NM_003106. Sox2 polypeptides, e.g. those that are at least 70%, 75%, 80%, 85%, 90%, 91%, 92%, 95%, 97%, 99%, or 100% identical to the sequence provided in GenBank Accession No. NM_003106. The nucleic acids that encode them find use as a reprogramming factor in the present invention.

By "pluripotency" and pluripotent stem cells it is meant that such cells have the ability to differentiate into all types of cells in an organism. The term "induced pluripotent stem cell" encompasses pluripotent cells, that, like embryonic stem (ES) cells, can be cultured over a long period of time while maintaining the ability to differentiate into all types of cells in an organism, but that, unlike ES cells (which are derived from the inner cell mass of blastocysts), are derived from differentiated somatic cells, that is, cells that had a narrower, more defined potential and that in the absence of experimental manipulation could not give rise to all types of cells in the organism. By "having the potential to become iPS cells" it is meant that the differentiated somatic cells can be induced to become, i.e. can be reprogrammed to become, iPS cells. In other words, the somatic cell can be induced to redifferentiate so as to establish cells having the morphological characteristics, growth ability and pluripotency of pluripotent cells. iPS cells have an hESC-like morphology, growing as flat colonies with large nucleo-cytoplasmic ratios, defined borders and prominent nuclei. In addition, iPS cells express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. In addition, the iPS cells are capable of forming teratomas. In addition, they are capable of forming or contributing to ectoderm, mesoderm, or endoderm tissues in a living organism.

The terms "primary cells", "primary cell lines", and "primary cultures" are used interchangeably herein to refer to cells and cell cultures that have been derived from a subject and allowed to grow in vitro for a limited number of passages, i.e. splittings, of the culture. For example primary cultures are cultures that may have been passaged 0 times, 1 time, 2 times, 4 times, 5 times, 10 times, or 15 times, but not enough times go through the crisis stage.

Starting cell population. As used herein, a "starting cell population", or "initial cell population" refers to a somatic cell, usually a primary, or non-transformed, somatic cell, which undergoes nuclear reprogramming by the methods of the invention. The starting cell population may be of any mammalian species, but particularly including human cells. Sources of starting cell populations include individuals desirous of cellular therapy, individuals having a genetic defect of interest for study, and the like.

In some embodiments, human cells obtained from a subject for the purpose of nuclear reprogramming may be chosen from any human cell type, including fibroblast cells, adipose tissue cells, mesenchymal cells, bone marrow cells, stomach cells, liver cells, epithelial cells, nasal epithelial cells, mucosal epithelial cells, follicular cells, connective tissue cells, muscle cells, bone cells, cartilage cells, gastrointestinal cells, splenic cells, kidney cells, lung cells, testicular cells, nervous tissue cells, etc. In some embodiments, the human cell type is a fibroblast, which may be conveniently obtained from a subject by a punch biopsy. In certain embodiments, the cells are obtained from subjects known or suspected to have a copy number variation (CNV) or mutation of the gene of interest. In other embodiments, the cells are from a patient presenting with idiopathic/sporadic form of the disease. In yet other embodiments, the cells are from a non-human subject. The cells are then reprogrammed, and may be transdifferentiated to adopt a specific cell fate, such as endodermal cells, neuronal cells, for example dopaminergic, cholinergic, serotonergic, GABAergic, or glutamatergic neuronal cell; pancreatic cells, e.g. islet cells, muscle cells including without limitation cardiomyocytes, hematopoietic cells, and the like.

The term "efficiency of reprogramming" may be used to refer to the ability of a cells to give rise to iPS cell colonies when contacted with reprogramming factors. Somatic cells that demonstrate an enhanced efficiency of reprogramming to pluripotentiality will demonstrate an enhanced ability to give rise to iPS cells when contacted with reprogramming factors relative to a control. The term "efficiency of reprogramming" may also refer to the ability of somatic cells to be reprogrammed to a substantially different somatic cell type, a process known as transdifferentiation. The term "efficiency of reprogramming" may also refer to the extent of telomere extension when reprogramming a cell from a senescent to a juvenile form. The efficiency of reprogramming with the methods of the invention vary with the particular combination of somatic cells, method of introducing reprogramming factors, and method of culture following induction of reprogramming.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "individual," "subject," "host," and "patient," are used interchangeably herein and refer to any mammalian subject for whom diagnosis, treatment, or therapy is desired, particularly humans.

Methods of Inducing Pluripotency in Vitro

A starting population of somatic cells are contacted with a population of mmRNA encoding reprogramming factors, as defined above, in a combination and quantity sufficient to reprogram the cell to pluripotency prior to, concurrent with or following activation of the somatic cell with an effective dose of an activator of innate immunity, where the activator of innate immunity is provided 5' triphosphate present on at least a portion of the mmRNA, or alternatively is provided as an additional agent. In one embodiment of the invention, the TLR is TLR3 or PKR. In some embodiments the TLR agonist is a double-stranded RNA or analog thereof. Reprogramming factors may be provided to the somatic cells individually or as a single composition, that is, as a premixed composition, of reprogramming factors.

In some embodiments, the starting population of cells is contacted with an effective dose of a mmRNA composition of the composition, comprising at least a portion of the population with a 5' triphosphate as described above. As known in the art, repeated transfections are typically required, at least 2, at least 3, at least 4, at least 5, at least 6, at least 7, at least 8, at least 9, at least 10 transfections, which can be repeated daily, seemi-daily, every two days, etc.

In other embodiments a conventional population of mmRNA, i.e. lacking 5' triphosphate, can be administered with an activator of innate immunity, e.g. a TLR or PKR agonist, e.g. LPS, dsRNA, etc., in a dose that is functionally equivalent to a dose of from 5 ng/ml to 3000 ng/ml poly I:C, and maintained in culture in the presence of such an agonist from a period of time from about 4 to about 18 days, e.g. from about 5 to about 10 days, and may be around 6 to 8 days.

The mmRNA encoding reprogramming factors may be added to the subject cells simultaneously or sequentially at different times, and may be added in combination with an additional activator of innate immunity and/or comprising 5' triphosphate on at least a portion of the mmRNA. In some embodiments, a set of at least three mRNA encoding reprogramming factors is added, e.g., Oct3/4, Sox2, and Klf4, c-myc, nanog or lin28. In some embodiments, a set of at least four mRNA encoding reprogramming factors is provided to the cells e.g., Oct3/4, Sox2, Klf4 and c-Myc; or Oct3/4, Sox2, lin28 and nanog. In some embodiments a set of five mRNA encoding reprogramming factors is provided to the cells, e.g. Oct3/4, Sox2, Klf4, c-Myc and lin28 or nanog.

Methods for introducing the mmRNA encoding reprogramming factors to somatic cells include transfection, lipofection, electroporation, exosomal delivery and the like, as known in the art. Following introduction of the mmRNA, cells are incubated for about 30 minutes to about 72 hours, e.g., 2 hours, 4 hours, 8 hours, 12 hours, 18 hours, 24 hours 36 hours, 48 hours, 60 hours, 72 hours, or any other period from about 30 minutes to about 72 hours. The reprogramming factors may be provided to the subject cells for about one to about 4 weeks, e.g. from about two to about 3 weeks.

The dose of mmRNA encoding reprogramming factors will vary with the nature of the cells, the factors, the culture conditions, etc. In some embodiments the dose will be from about 1 nM to about 1 µM for each factor, more usually from about 10 nM to about 500 nM, or around about 100 to 200 nM. In embodiments where an additional activator is used, the cells are initially exposed during exposure to the reprogramming actors for at least about 1 day, at least about 2 days, at least about 4 days, at least about 6 days or one week, and may be exposed for the entire reprogramming process, or less. The dose will depend on the specific agonist, but may be from about 1 ng/ml to about 1 µg/ml, from about 10 ng/ml to about 500 ng/ml.

Following introduction of reprogramming factors, the somatic cells may be maintained in a conventional culture medium comprising feeder layer cells, or may be cultured in the absence of feeder layers, i.e. lacking somatic cells other than those being induced to pluripotency. Feeder layer free cultures may utilize a protein coated surface, e.g. matrigel, etc.

iPS cells induced to become such by the methods of the invention have an hESC-like morphology, growing as flat colonies with large nucleo-cytoplasmic ratios, defined borders and prominent nuclei. In addition, the iPS cells may express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. In addition, the iPS cells are capable of forming teratomas. In addition, they are capable of forming or contributing to ectoderm, mesoderm, or endoderm tissues in a living organism.

Genes may be introduced into the somatic cells or the iPS cells derived therefrom for a variety of purposes, e.g. to replace genes having a loss of function mutation, provide marker genes, etc. Alternatively, vectors are introduced that express antisense mRNA or ribozymes, thereby blocking expression of an undesired gene. Other methods of gene therapy are the introduction of drug resistance genes to enable normal progenitor cells to have an advantage and be subject to selective pressure, for example the multiple drug resistance gene (MDR), or anti-apoptosis genes, such as bcl-2. Various techniques known in the art may be used to introduce nucleic acids into the target cells, e.g. electroporation, calcium precipitated DNA, fusion, transfection, lipofection, infection and the like, as discussed above. The particular manner in which the DNA is introduced is not critical to the practice of the invention.

The iPS cells produced by the above methods may be used for reconstituting or supplementing differentiating or differentiated cells in a recipient. The induced cells may be differentiated into cell-types of various lineages. Examples of differentiated cells include any differentiated cells from ectodermal (e.g., neurons and fibroblasts), mesodermal (e.g., cardiomyocytes), or endodermal (e.g., pancreatic cells) lineages. The differentiated cells may be one or more: pancreatic beta cells, neural stem cells, neurons (e.g., dopaminergic neurons), oligodendrocytes, oligodendrocyte progenitor cells, hepatocytes, hepatic stem cells, astrocytes, myocytes, hematopoietic cells, or cardiomyocytes.

There are numerous methods of differentiating the induced cells into a more specialized cell type. Methods of differentiating induced cells may be similar to those used to differentiate stem cells, particularly ES cells, MSCs, MAPCs, MIAMI, hematopoietic stem cells (HSCs). In some cases, the differentiation occurs ex vivo; in some cases the differentiation occurs in vivo.

The induced cells, or cells differentiated from the induced cells, may be used as a therapy to treat disease (e.g., a genetic defect). The therapy may be directed at treating the cause of the disease; or alternatively, the therapy may be to treat the effects of the disease or condition. The induced cells may be transferred to, or close to, an injured site in a subject; or the cells can be introduced to the subject in a manner allowing the cells to migrate, or home, to the injured site. The transferred cells may advantageously replace the damaged or injured cells and allow improvement in the overall condition of the subject. In some instances, the transferred cells may stimulate tissue regeneration or repair.

The transferred cells may be cells differentiated from induced cells. The transferred cells also may be multipotent stem cells differentiated from the induced cells. In some cases, the transferred cells may be induced cells that have not been differentiated.

The number of administrations of treatment to a subject may vary. Introducing the induced and/or differentiated cells into the subject may be a one-time event; but in certain situations, such treatment may elicit improvement for a limited period of time and require an on-going series of repeated treatments. In other situations, multiple administrations of the cells may be required before an effect is observed. The exact protocols depend upon the disease or condition, the stage of the disease and parameters of the individual subject being treated.

The cells may be introduced to the subject via any of the following routes: parenteral, intravenous, intraarterial, intramuscular, subcutaneous, transdermal, intratracheal, intraperitoneal, or into spinal fluid.

The iPS cells may be administered in any physiologically acceptable medium. They may be provided alone or with a suitable substrate or matrix, e.g. to support their growth and/or organization in the tissue to which they are being transplanted. Usually, at least $1\times10^5$ cells will be administered, preferably $1\times10^6$ or more. The cells may be introduced by injection, catheter, or the like. The cells may be frozen at liquid nitrogen temperatures and stored for long periods of time, being capable of use on thawing. If frozen, the cells will usually be stored in a 10% DMSO, 50% FCS, 40% RPMI 1640 medium. Once thawed, the cells may be expanded by use of growth factors and/or stromal cells associated with progenitor cell proliferation and differentiation.

Methods of Inducing Transdifferentiation In Vitro or In Vivo

Transdifferentiation, as defined above, is the nuclear reprogramming of a somatic cell to a substantially different somatic cell, for example a somatic cell of a different lineage. Examples of transdifferentiation include, without limitation: fibroblast→myocyte; fibroblast→endothelial cell; fibroblast→neural cell; fibroblast→islet cell; fibroblast→hematopoietic cell; etc.; adipose tissue cell to any one of myocytes, endothelial cell, neural cell, hematopoietic cell, islet cell, etc.; and the like. Cells suitable as a starting populations have been defined above. This methodology can provide for consistency and practical application in regenerative medicine.

For the purpose of transdifferentiation, a different set of factors and media specific to the derived cell phenotype, will be used. In some embodiments the cell is exposed to an activator of innate immunity in the presence of mmRNA encoding lineage specific reprogramming factors. In some embodiments, innate immunity is activated in the absence of lineage specific reprogramming factors, but in the presence of growth factors and/or small molecules which promote transdifferentiation to the desired somatic cell. In some embodiments, the starting population of cells is contacted with an effective dose of a TLR agonist, e.g. LPS, dsRNA, etc., in a dose that is functionally equivalent to a dose of from 5 ng/ml to 3000 ng/ml poly I:C, and maintained in culture in the presence of such an agonist from a period of time from about 4 to about 18 days, e.g. from about 5 to about 10 days, and may be around 6 to 8 days. Following induction of innate immunity by this process, the cells is exposed to one or a cocktail of mmRNA encoding lineage specific reprogramming factors.

For example, following TLR agonist treatment with an effective dose for about one week, cells are transdifferentiated by exposing them to mmRNA encoding differentiating factors for an additional one to four weeks. The medium may be replaced with fresh medium supplemented with growth factors specific for the cell being derived. The appropriate concentration of the factors required is determined by conducting a dose-response curve. Similarly, the transdifferentiated cells are characterized with a series of standard secondary assays including gene expression, morphological and functional analysis. In many embodiments, culture protocols used for differentiation of a somatic cell type from a pluripotent cell population, e.g. ES cells, iPS cells, etc. can be applied to transdifferentiation. That is, a cell that has been exposed to a TLR agonist in culture for a period of time sufficient to induce innate immunity can then be exposed to a conventional set of factors for lineage specific differentiation.

The cells may be differentiated into cell-types of various lineages. Examples of transdifferentiated cells include any differentiated cells from ectodermal (e.g., neurons and fibroblasts), mesodermal (e.g., cardiomyocytes), or endodermal (e.g., endodermal cells, pancreatic cells) lineages. The transdifferentiated cells may be one or more: pancreatic beta cells, neural stem cells, neurons (e.g., dopaminergic neurons), oligodendrocytes, oligodendrocyte progenitor cells, hepatocytes, hepatic stem cells, astrocytes, myocytes, hematopoietic cells, endodermal cells, or cardiomyocytes, etc.

The transdifferentiated cells may be terminally differentiated cells, or they may be capable of giving rise to cells of a specific lineage. For example, cells can be differentiated into a variety of multipotent cell types, e.g., neural stem cells, cardiac stem cells, or hepatic stem cells. The stem cells may then be further differentiated into new cell types, e.g., neural stem cells may be differentiated into neurons; cardiac stem cells may be differentiated into cardiomyocytes; and hepatic stem cells may be differentiated into hepatocytes.

There are numerous methods of differentiating the induced cells into a more specialized cell type. Methods of differentiating induced cells may be similar to those used to differentiate stem cells, particularly ES cells, MSCs, MAPCs, MIAMI, hematopoietic stem cells (HSCs). In some cases, the differentiation occurs ex vivo; in some cases the differentiation occurs in vivo.

In some cases, sub-populations of transdifferentiated somatic cells may be purified or isolated. In some cases, one or more monoclonal antibodies specific to the desired cell type are incubated with the cell population and those bound cells are isolated. In other cases, the desired subpopulation of cells expresses a reporter gene that is under the control of a cell type specific promoter.

The transdifferentiated cells may be used as a therapy to treat disease (e.g., a genetic defect). The therapy may be directed at treating the cause of the disease; or alternatively, the therapy may be to treat the effects of the disease or condition. The transdifferentiated cells may be transferred to, or close to, an injured site in a subject; or the cells can be introduced to the subject in a manner allowing the cells to migrate, or home, to the injured site. The transferred cells may advantageously replace the damaged or injured cells and allow improvement in the overall condition of the subject. In some instances, the transferred cells may stimulate tissue regeneration or repair.

The number of administrations of treatment to a subject may vary. Introducing the induced and/or differentiated cells into the subject may be a one-time event; but in certain situations, such treatment may elicit improvement for a limited period of time and require an on-going series of repeated treatments. In other situations, multiple administrations of the cells may be required before an effect is observed. The exact protocols depend upon the disease or condition, the stage of the disease and parameters of the individual subject being treated.

The cells may be introduced to the subject via any of the following routes: parenteral, intravenous, intraarterial, intramuscular, subcutaneous, transdermal, intratracheal, intraperitoneal, or into spinal fluid.

The transdifferentiated cells may be transferred to subjects suffering from a wide range of diseases or disorders. Subjects suffering from neurological diseases or disorders could especially benefit from cell therapies. In some approaches, the transdifferentiated cells are neural stem cells or neural cells transplanted to an injured site to treat a neurological condition, e.g., Alzheimer's disease, Parkinson's disease, multiple sclerosis, cerebral infarction, spinal cord injury, or other central nervous system disorder, see, e.g., Morizane et al., (2008), Cell Tissue Res., 331(1):323-326; Coutts and Keirstead (2008), Exp. Neurol., 209(2):368-377; Goswami and Rao (2007), Drugs, 10(10):713-719. Degenerative heart diseases such as ischemic cardiomyopathy, conduction disease, and congenital defects could benefit from stem cell therapies, see, e.g. Janssens et al., (2006), Lancet, 367:113-121. Endothelial cells are useful in improving vascular structure and function, enhancing angiogenesis, and improving perfusion, e.g. in peripheral arterial disease. Pancreatic islet cells (or primary cells of the islets of Langerhans) may be transplanted into a subject suffering from diabetes (e.g., diabetes mellitus, type 1), see e.g., Burns et al., (2006) Curr. Stem Cell Res. Ther., 2:255-266. In some embodiments, pancreatic beta cells derived from the methods of the invention cells may be transplanted into a subject suffering from diabetes (e.g., diabetes mellitus, type 1). In other examples, hepatic cells or hepatic stem cells derived from induced cells are transplanted into a subject suffering from a liver disease, e.g., hepatitis, cirrhosis, or liver failure.

Hematopoietic cells or hematopoietic stem cells (HSCs) may be transplanted into a subject suffering from cancer of the blood, or other blood or immune disorder. Examples of cancers of the blood that are potentially treated by hematopoietic cells or HSCs include: acute lymphoblastic leukemia, acute myeloblastic leukemia, chronic myelogenous leukemia (CML), Hodgkin's disease, multiple myeloma, and non-Hodgkin's lymphoma. Often, a subject suffering from such disease must undergo radiation and/or chemotherapeutic treatment in order to kill rapidly dividing blood cells. Introducing HSCs derived from the methods of the invention to these subjects may help to repopulate depleted reservoirs of cells. In some cases, hematopoietic cells or HSCs derived by transdifferentiation may also be used to directly fight cancer. For example, transplantation of allogeneic HSCs has shown promise in the treatment of kidney cancer, see, e.g., Childs et al., (2000), N. Engl. J. Med., 343:750-758. In some embodiments, allogeneic, or even autologous, HSCs derived from induced cells may be introduced into a subject in order to treat kidney or other cancers. Hematopoietic cells or HSCs derived from induced cells may also be introduced into a subject in order to generate or repair cells or tissue other than blood cells, e.g., muscle, blood vessels, or bone. Such treatments may be useful for a multitude of disorders.

In some embodiments, the cells are transdifferentiated in vivo. In other words, the cocktail of transdifferentiating factors is administered to the host, so as to therapeutically modify cell phenotype in vivo. For example, a transdifferentiation cocktail of growth factors and/or small molecules is administered in the setting of innate immune activation so as to generate a therapeutic cell. For example, in a patient with heart damage, one might provide a cocktail of such factors that would generate a cardiovascular cell from a cardiac fibroblast.

In some embodiments, the cells are exposed to an activator of innate immunity, and proteins to enhance telomere extension, e.g. telomerase. In the case of mmRNA encoding telomerase, conveniently the activator of innate immunity is the mmRNA that encodes the telomerase protein. As described above, the mmRNA will be designed to provide the optimal level of innate immune activation to have the desired effect.

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention, which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the reagents, cells, constructs, and methodologies that are described in the publications, and which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Example 1

Activation of Innate Immunity Enhances the Effect of RNA Treatment

We have found that activation of innate immunity is essential for efficient nuclear reprogramming. During reprogramming of cells with modified mRNA, it was found that retaining the 5' triphosphate in at least a portion of artificially synthesized RNA constructs is important for efficient mmRNA-based reprogramming of fibroblasts to induced pluripotent stem cells.

Mammalian cells contain RNA sensors that activate the innate immune system. Activation of innate immunity can cause inflammation or apoptosis. Accordingly, in an attempt to substantially reduce the activation of innate immunity, investigators have modified therapeutic RNA by incorporating modified nucleosides, and by removing the 5' triphosphate of the synthesized RNA. Innate immune activation, through the human TLR3, TLR7, and TLR8 receptors; or through the PKR (protein kinase R) pathway is thereby reduced. See, for example, Kariko et al. (2005) Immunity 23(2):165-175; and Warren et al. (2010), supra.

However, we have found that a substantial activation of the innate immune response is needed to have optimal effects in some cases. In particular, we have shown that the use of mmRNA for reprogramming of somatic cells to iPSCs (induced pluripotent stem cells) requires the activation of TLR3 for maximal effect. Activation of innate immunity causes global changes in epigenetic modifiers that place the chromatin into an "open configuration". This effect of innate immune activation facilitates the action of the transcriptional factors encoded by mmRNA.

In addition to using modified nucleotides to suppress innate immune activation, some groups have treated the mmRNA with both cotranscriptional capping, and phosphatase to remove 5' triphosphates. These 5' triphosphates can be detected by RNA-dependent protein kinase (PKR), which is cellular sensor that activates innate immune pathways and global repression of protein translation (Nallagatla and Bevilacqua (2008) RNA 14(6):1201-13). Conventional protocols for generating iPSCs using mmRNA include the use of phosphatase treated mmRNA.

We have found that this method of reducing innate immune activation actually reduces the efficacy of the mmRNA in generating iPSCs. In keeping with conventional protocols, phosphatase was used to remove the 5' triphosphates from mmRNA (PhT-mmRNA) encoding the five reprogramming factors (OKSML; Oct 4, KLF4, Sox2, cMyc and Lin28). In another set of reagents we omitted phosphatase treatment (nPhT-mmRNA).

nPhT- and PhT-mmRNAs mmRNA generation. As shown in FIG. 1, plasmid pTM1 was described previously (B. Moss et al., Nature, Vol 348, 1990] and was modified to yield pJRG-3s, by the substitution of the sequence between XbaI/SalI sites on a sequence containing the T7 promoter, the 5' UTR of human beta globin (hBB), the GFP open reading frame linked by SpeI/MfeI cloning site, the 3' UTR of hBB, a 151 bp poly-A sequence, and a restriction site for linearization with class IIs enzyme following the poly-A sequence (FIG. 1). To clone cDNA of reprogramming factors into pJRG-3s, the GFP coding region was excised from pJRG-3s with SpeI/MfeI enzymes and replaced by the coding sequences of Oct4, Klf4, Sox2, cMyc or Lin28 (O,K,S,M,L) respectively. cDNAs were amplified by polymerase chain reaction from the respective plasmids (Addgene Cat #16579, 16580, 16577, 16578, 17219) using high fidelity DNA polymerase (Invitrogen) and primers that include on their 5' the SpeI and MfeI sequences for cloning into pJRG-3s after GFP excision.

Each resulting intermediate plasmid was bi-directionally sequenced to ensure fidelity, and then linearized and transcribed to capped modified mRNA (mmRNA) using the RNA polymerase from the MEGAscript T7 Kit (Ambion,) and a custom nucleotide mix of canonical and modified nucleotides (TriLink BioTechnologies) in which the final nucleotide concentrations per 40 µl IVT reaction were 7.5 mM for each of adenosine-5'-triphosphate (ATP), 5-methylcytidine-5'-triphosphate (m5C), and pseudouridine-5'-triphosphate ($\Psi$), 1.5 mM for guanosine-5'-triphosphate (GTP), and 6 mM for the cap analog (ARCA, NEB), or a molar ratio of ATP:m5C:$\Psi$:GTP:ARCA of 1:1:1:0.2:0.8. RNA was purified with MEGAclear spin columns (Ambion) and divided into two aliquots. Of them, one aliquot was treated with Antarctic Phosphatase (New England Biolabs). The other, to save residual 5'-triphosphates, was omitted from the phosphatase treatment. Treated RNA was repurified, and the size and integrity of all mRNA products was verified using denaturing agarose gel electrophoresis.

BJ human neonatal foreskin fibroblasts were obtained from ATCC and newborn human foreskin fibroblasts (NuFF) feeder cells mitomycin-C treated from GlobalStem Cells were cultivated on High Glucose DMEM supplemented with 10% Heat-inactivated Fetal Bovine Serum and PenStrep (1:100). The $2 \times 10^4$ of BJ fibroblasts were plated on $2.5 \times 10^5$ NuFFs feeder and subjected for reprogramming.

The OKSML mmRNA reprogramming cocktail was prepared by pooling individual RNA stocks to produce 100 ng/µl blend with equal molarity for each component except for OCT4 included at 3×molar concentration. The $2.0 \times 10^4$ BJ fibroblasts plated on $2.5 \times 10^5$ NuFFs feeder were transfected with 1.2 µg of OKSML cocktail per well of 6-well plate using Lipofectamine RNAiMax (Invitrogen), following manufacturer instructions. Transfection was performed on Pluriton medium (Stemgent) supplemented with Pluriton supplement (Stemgent) and 200 ng/mL B18R (eBioscience). Media was replaced 4 hrs post transfection. Usually ten consecutive transfections were performed 24 h apart. The experiment was executed in ambient oxygen and 5% $CO_2$.

Figure 4E:
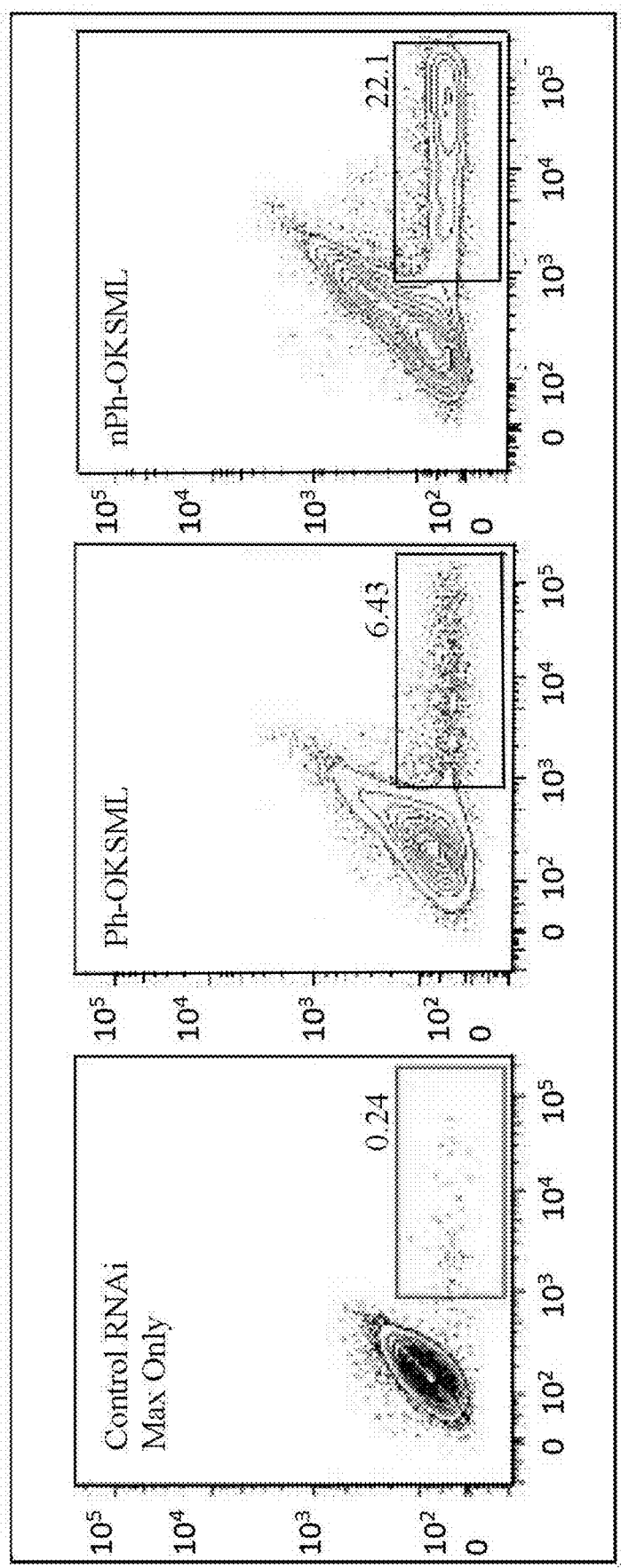

BJ-FBs were daily transfected 10 times with nPhT and PhT-OKSML-mmRNA. After 10 transfections, cells were live stained with 5 µg/ml StainAlive DyLight 488 TRA-1-60 antibody (Stemgent) and efficiency of reprogramming was evaluated using fluorescent microscopy and FACS. Shown in FIG. 4, (A,B,C,D) Immunofluorescent analysis of pluripotent marker TRA-1-60 (A) Bright Field (BF), (B) TRA1-60 positive cells on day 10 after reprogramming with PhT OKSML-mmRNA Mag ×20 and (B) BF, (C) TRA1-60 positive cells on day 10 after reprogramming with nPhT OKSML-mmRNA Mag ×20. Immediately after fluorescent microscopy cells were trypsinized and FACS sorted (Becton Dickinson) for TRA-1-60 positive cells. A typical FACS plot (E) demonstrates increased the frequency of reprogrammed cells expressing TRA-1-60 marker with nPh-OKSML mmRNA (number indicate %). F) Quantitative data of FACS sorting. The data represented as mean±s.d., n=3. We found that omitting the phosphatase treatment significantly increased the efficiency of reprogramming of human fibroblasts.

Figure 5:
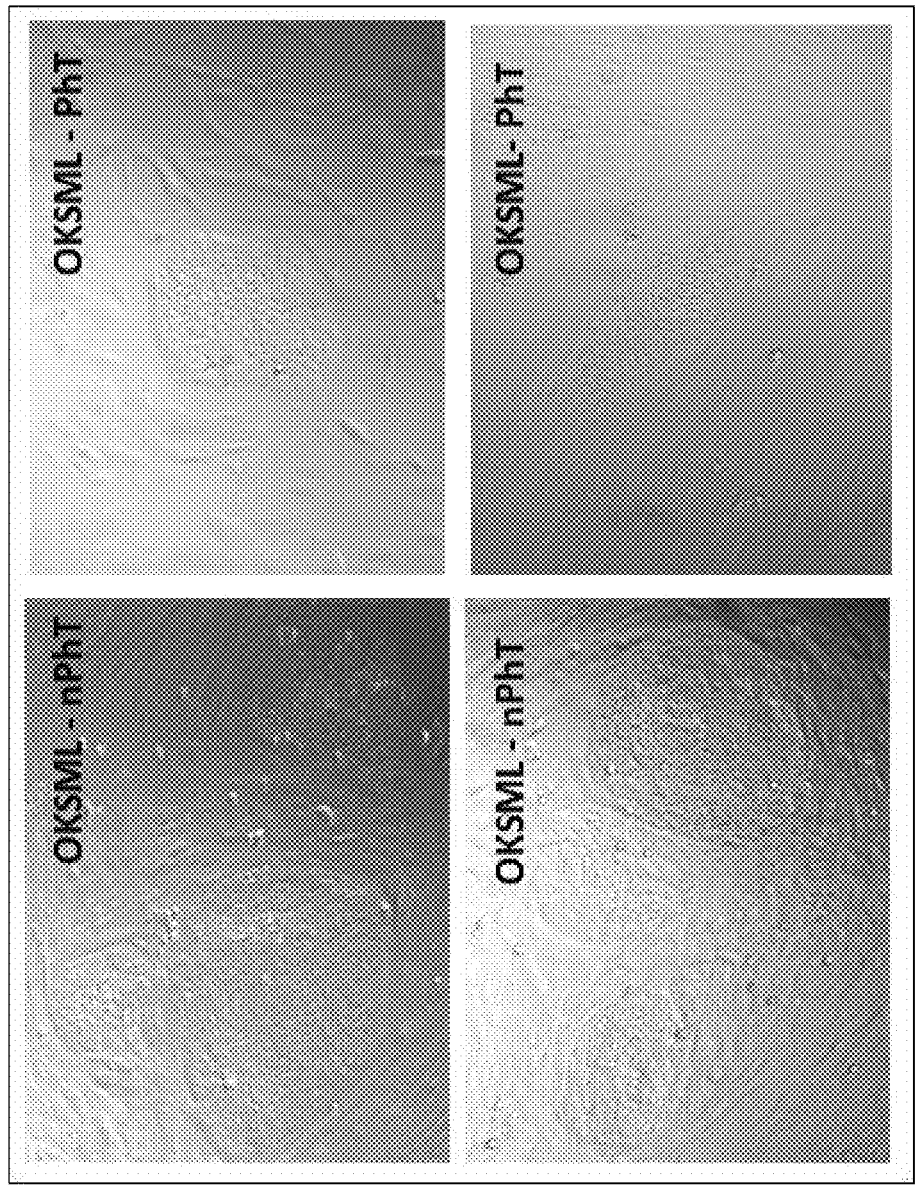
FIG. 5. RNA induced pluripotent cells (RiPS, Passage #1/Day8) derived after 10 transfections from $2\times10^3$ FACS sorted TRA-1-60 positive cells plated in well of 96 well plate.

As shown in FIG. 5, reprogramming of BJ-FBs with nPhT OKSML mmRNA is more efficient and yields on day 18 (8 days on matrigel) after first transfection primary RiPS colonies with more mature morphology.

These data demonstrate that activation of innate immunity is required for optimal nuclear reprogramming using mmRNA. Efficiency of reprogramming increased by using mmRNAs comprising an intact 5' triphosphate group. Furthermore, the use of mmRNA for modifying cell signaling and/or cell fate is improved using mmRNAs comprising an intact 5' triphosphate. More broadly, we show that substantial activation of innate immunity by mmRNA is a requirement of optimal cellular modification by mmRNA.

Example 2. Importance of Innate Immune Signaling in Telomere Extension

Human Endothelial cells are cultivated on complete medium and at Passage 14 pretreated with different NF-κB and PKR inhibitors. Subsequently, cells are transfected with hTERT or p-hTERT mmRNAs using Lipofectomin RNiMax for a total of three transfections at 48-hour intervals. Two days after the third treatment all treated cells and controls are harvested, genomic DNA prepared and lengthening of telomeres quantified by monochrome multiplex qPCR method (MMqPCR). In some cases, the cells are treated with inhibitors of PKR, or inhibitors of elements downstream of PKR signaling pathway such as NF-κB. Treatment with hTERT or p-hTERT mmRNAs increased telomere length and population doublings, an effect that was reduced by inhibitors of PKR or nFkB. These studies indicate that telomere extension using mmRNA encoding telomerase benefits from activation of innate immune signaling for optimal effect.

What is claimed is:

1. A method of nuclear reprogramming of mammalian somatic cells, the method comprising:
   contacting a population of the mammalian somatic cells with:
   an effective dose of an innate immune response activator; and
   a population of modified mRNA (mmRNA), wherein at least 1% of the mmRNA population comprises 5' triphosphate encoding a cocktail of reprogramming or transcriptional factors.

2. The method of claim 1, wherein the reprogramming of the mammalian somatic cells comprises reprogramming the mammalian somatic cells from a senescent form.

3. The method of claim 2, wherein the cocktail of reprogramming or transcriptional factors comprises growth factors that support nuclear reprogramming.

4. The method of claim 2, wherein the cocktail of reprogramming or transcriptional factors comprises small molecules that support nuclear reprogramming from a senescent form.

5. The method of claim 1, wherein the innate immune response activator is provided by the mmRNA itself.

6. The method of claim 1, wherein the innate immune response activator is a TLR3 or TLR4 agonist.

7. The method of claim 6, wherein the TLR3 or TLR4 agonist is a double stranded RNA or analog thereof.

8. The method of claim 7, wherein the TLR3 or TLR4 agonist is polyinosine-polycytidylic acid (poly(I:C)).

9. The method of claim 1, wherein the cocktail of reprogramming or transcriptional factors comprises hTERT.

10. The method of claim 1, wherein contacting the mammalian somatic cells with the effective dose of the innate immune response activator and the population of mmRNA is performed in vivo.

11. The method of claim 1, wherein contacting the mammalian somatic cells with the effective dose of the innate immune response activator and the population of mmRNA is performed in vitro.

12. The method of claim 1, wherein the mammalian somatic cells are human cells.

* * * * *